(12) United States Patent
Mohapatra et al.

(10) Patent No.: US 9,782,494 B2
(45) Date of Patent: *Oct. 10, 2017

(54) METHODS OF USING MULTILAYER MAGNETIC MICELLE COMPOSITIONS

(71) Applicant: University of South Florida, Tampa, FL (US)

(72) Inventors: Subhra Mohapatra, Tampa, FL (US); Shyam S. Mohapatra, Tampa, FL (US); Mahasweta Das, Wesley Chapel, FL (US); Chunyan Wang, Tampa, FL (US)

(73) Assignee: University of South Florida, Tampa, FL (US)

( * ) Notice: Subject to any disclaimer, the term of this patent is extended or adjusted under 35 U.S.C. 154(b) by 1123 days.

This patent is subject to a terminal disclaimer.

(21) Appl. No.: 13/773,718

(22) Filed: Feb. 22, 2013

(65) Prior Publication Data
US 2013/0230595 A1 Sep. 5, 2013

Related U.S. Application Data

(60) Provisional application No. 61/602,319, filed on Feb. 23, 2012.

(51) Int. Cl.
*A61K 48/00* (2006.01)
*A61K 31/7088* (2006.01)
*A61K 9/00* (2006.01)
*A61K 9/51* (2006.01)

(52) U.S. Cl.
CPC ............ *A61K 48/00* (2013.01); *A61K 9/0009* (2013.01); *A61K 9/0043* (2013.01); *A61K 9/5115* (2013.01); *A61K 31/7088* (2013.01); *A61K 48/0075* (2013.01)

(58) Field of Classification Search
CPC .. A61K 48/0075; A61K 48/00; A61K 9/5115; A61K 9/0009; A61K 9/0043; A61K 31/7088
See application file for complete search history.

(56) References Cited

U.S. PATENT DOCUMENTS

| 6,824,780 | B1 | 11/2004 | Devaux | |
|---|---|---|---|---|
| 2004/0096881 | A1 | 5/2004 | Blasko | |
| 2011/0002851 | A1* | 1/2011 | Haas | A61K 9/0019 424/9.1 |
| 2011/0020239 | A1 | 1/2011 | Bulte | |
| 2011/0129525 | A1 | 6/2011 | Rasschaert | |

OTHER PUBLICATIONS

Hua Ai et al.,Adv. Matter, 2005, 17, 1949-1952.*
Dhananjay Jere et al., International J. of Pharmaceutics, 378, 194-200, 2009.*
M. Conese, et al. Gene and cell therapy for cystic fibrosis: from bench to bedside, Journal of Cystic Fibrosis, 2011, 10, S114-S128.
M. L. Edelstein et al., Gene therapy clinical trials worldwide to 2007—an update, Journal of Gene Medicine 2007, 9, 833.
C. E. Thomas et al., Progress and Problems with the Use of Viral Vectors for Gene Therapy, Nature Reviews Genetics 2003, 4, 346.
J. F. Guo et al., Can non-viral technologies knockdown the barriers to siRNA delivery and achieve the next generation of cancer therapeutics? Biotechnology Advances 2011, 29, 402-417.
C. H. Chang et al., Engineering of *Escherichia coli* for Targeted delivery of Transgenes to HER2/neu-Positive Tumor Cells, Biotechnology and Bioengineering, 2011, 1662-1672, vol. 108.
Y. A. Chen et al., A gene delivery system based on the N-terminal domain of human topoisomerase I, Biomaterials 2011(32): pp. 4174-4184.
C. M. McIntosh, et al., Inhibition of DNA Transcription Using Cationic Mixed Monolayer Protected Gold Clusters, Journal of the American Chemical Society 2001, vol. 123, 7626-7629.
G. Han et al., Stability of Gold Nanoparticle-Bound DNA toward Biological, Physical, and Chemical Agents, Chemical Biology & Drug Design 2006, 67, 78.
G. Han et al., Controlled Recovery of the Transcription of Nanoparticle-Bound DNA by Intracellular Concentrations of Glutathione, Bioconjugate Chemistry 2005, 16, 1356.
L.Z. Gao et al., Carbon Nanotube Delivery of the GFP Gene into Mammalian Cells, Chembiochem 2006, 7, 239-242.
U. Lungwitz et al., Eur. J. of Pharmaceutics and Biopharmaceutics 2005, 60, 247.
T. L. Kaneshiro et al., Synthesis, Characterization, and Gene Delivery of Poly-L-lysine Octa(3-aminopropyl_silsesquioxane Dendrimers, Molecular Pharmaceutics 2007, 4, 759.
K. Corsi et al., Mesenchymal stem cells, MG63 and HEK293 transfection using chitosan-DNA nanoparticles, Biomaterials 2003, vol. 24, 1255.
J. Dennig, Gene Transfer in Eukaryotic Cells Using Activated Dendrimers, Applications in Materials and Life Sciences 2003, 228, 227.
H. M. Wu et al., A serum-resistant polyamidoamine-based polypeptide dendrimer for gene transfection, Biomaterials 2011, 32, 1619.
M. Morille et al., Biomaterials 2006, 29, 3477.
H. L. Jiang et al., Chitosan-graft-polyethylenimine as a gene carrier, Journal of Controlled Release 2007, 117, 273.
M. Breunig et al., Proceedings of the National Academy of Sciences of the United States of America 2007, 104, 14454.
Lou, Y. L., et al., 2009, Poly(ethylene imine)-g-chitosan using EX-810 as a spacer for nonviral gene delivery vectors. J. Biomed Mater Res A 88:1058-1068.
D. Jere et al., 2009, Chitosan-graft-polyethylenimine for Akt1 siRNA delivery to lung cancer cells, International Journal of Pharmaceutics 2009, 378, 194.

(Continued)

*Primary Examiner* — Robert Cabral
(74) *Attorney, Agent, or Firm* — Thomas|Horstemeyer, LLP

(57) ABSTRACT

Provided herein is a method of transfecting a brain cell of a subject with a polynucleotide comprising systemically administering to the subject a composition comprising a micelle having a hydrophobic superparamagnetic iron oxide nanoparticle (SPION) core, a first coating comprising a cationic polymer, and a second coating comprising the polynucleotide, wherein the subject has a mild traumatic brain injury.

13 Claims, 7 Drawing Sheets

(56) References Cited

OTHER PUBLICATIONS

H. L. Jiang et al., Galactosylated chitosan-graft-polyethylenimine as a gene carrier for hepatocyte targeting, Gene Therapy 2007, 14, 1389.
H. L. Jiang et al., Gene delivery to Stem Cells by Combination of Chitosan-Graft-Polyethylenimine as a Gene Carrier and E-Cadherin-IgG Fc as an Extracellular Matrix, Journal of Biomedical Nanotechnology, 2007(3): 377-383.
P. Zou et al., Superparamagnetic Iron Oxide Nanotheranostics for Targeted Cancer Cell Imaging and pH-Dependent Intracellular Drug Release, Molecular Pharmaceutics 2010, 7, 1974.
R. Chen et al., Efficient nano iron particle-labeling and noninvasive MR imaging of mouse bone marrow-derived endothelial progenitor cells, International Journal of Nanomedicine 2011(6): 511-519.
F. M. Kievit et al., PEI-PEG-Chitosan-Copolymer-Coated Iron Oxide Nanoparticles for Safe Gene Delivery: Synthesis, Complexation, and Transfection, Advanced Functional Materials 2009, 19, 2244.
O. Veiseh et al., Chlorotoxin bound magnetic nanovector tailored for cancer cell targeting, imaging, and siRNA delivery, Biomaterials 2010, vol. 31, pp. 8032-8042.
G. Chen et al., Biomaterials, 2009, pp. 1962-1970, vol. 30.
N. Nasongkla et al., Nano Letters 2006, 6, 2427.
X. T. Shuai et al., Journal of Controlled Release 2004, 98, 41.
J. S. Guthi et al., MRI-Visible Micellar Nanomedicine for Targeted Drug Delivery to Lung Cancer Cells, Molecular Pharmaceutics 2010, 7, 32.
G. B. Hong et al., Folate-funtionalized polymeric micelle as hepatic carcinoma-targeted, MRI-uitrasensitive delivery system of antitumor drugs, Biomedical Microdevices 2008, 10, 693.
Wang C, Ravi S, Martinez GV, Chinnasamy V, Raulji P, Howell M, Davis Y, Mallela J, Seehra MS, Mohapatra S (2012) Dual-purpose magnetic micelles for MRI and gene delivery. J Control Release.
Lucke, A., et al., 2000, Biodegradable poly(D,L-lactic acid)-poly-ethylene glycol)-monomethyl ether diblock copolymers: structures and surface properties relevant to their use as biomaterials. Biomaterials 21: 2361-2370.
Sun S, Zeng H (2002) Size-controlled synthesis of magnetite nanoparticles, J Am Chem Soc 124:8204-8205.
M. Das et al., Lateral fluid percussion injury of the brain induces CCL20 inflammatory chemokine expression in rats, Journal of Neuroinflammation 2011, 8, 148.
Schmued LC, Albertson C, Slikker W, Jr. (1997) Fluoro-Jade: a novel fluorochrome for the sensitive and reliable histochemical localization of neuronal degeneration. Brain Res 751:37-46.
E. A. Duckworth et al., Temporary focal ischemia in the mouse: technical aspects and patterns on Fluoro-Jade evident neurodegeneration. Brain Research 2005, 1042, 29-36.
Al-Deen, F.N., et al., On designing stable magnetic vectors as carriers for malaria DNA vaccine. Colloids Surf B Biointerfaces, Feb. 1, 2013, 102C:492-503.
Al-Deen, F.N., et al., Superparamagnetic nanoparticles for effective delivery of malaria DNA vaccine. Langmuir, 2011, 27:7, 3703-3712.
Castillo, B., et al., Intracellular Delivery of siRNA by Polycationic Superparamagnetic Nanoparticles, J Drug Deliv., 2012, 2012:218940.
Cho, Y., et al., Chitosan produces potent neuroprotein and physiological recovery following traumatic spinal cord injury. J Exp. Biol., 2010, 213:1513-1520.
Dalby, B., et al., 2004, Advanced transfection with Lipofectamine 2000 reagent: primary neurons, siRNA, and high-throughput applications. Methods 22:95-103.
Ettenhofer, M. L., et al., A Comparison of Long-Term Postconcussive Symptoms between University Students with and without a History of Mild Traumatic Brain Injury or Orthopedic Injury. J. Int. Neuropsychol. Soc., May 2012, 18:3, 1-10.
Ettenhofer, M. L., et al,, 2009, The significance of mild traumatic brain injury to cognition and self-reported symptoms in long-term recovery from injury. J. Clin. Exp. Neuropsychol. 31:363-372.
Faul, M., et al., 2010, Traumatic brain injury in the United States: emergency department visits, hospitalizations, and deaths. Atlanta (GA): Centers for Disease Control and Prevention, National Center for Injury Prevention and Control.
Gersting, S. W., et al., 2004, Gene delivery to respiratory epithelial cells by magnetofection, J. Gene Med. 6:913-922.
Guerra-Crespo, M., et al., 2003, Polyethylenimine improves the transfection efficiency of primary cultures of post-mitotic rat fetal hypothalamic neurons. J Neurosci Methods 127: 179-192.
Halldorsson J. G., et al., The scope of early traumatic brain injury as a long-term health concern in two nationwide samples: prevalence and prognostic factors. Brain Inj., 2012, 26:1, 1-13.
Kabadi, S. V., et al., 2010, Fluid-percussion-induced-traumatic brain injury model in rats. Nature protocols 5:1552-1563.
McBain S. C., et al., 2008, Magnetic nanoparticles as gene delivery agents: enhanced transfection in the presence of oscillating magnet arrays. Nanotechnology 19:405102.
International Search Report and Written Opinion mailed Mar. 26, 2013 for U.S. Appl. No. 14/346,330.
Ozen, L. J., et al., 2012, Slowing down after a mild traumatic brain injury: a strategy to improve cognitive task performance? Arch Clin Neuropsychol 27:85-100.
Perez-Martinez, F. C., et al., 2009, Barriers to non-viral vector-mediated gene delivery in the nervous system, Pharm Res 28:1843-1858.
Plank C, Vlaskou D, Schillinger U, Mykhaylyk O., 2011, MagnetofectionTM platform: from magnetic nanoparticles to novel nucleic acid therapeutics, Ther Deliv 2:717-726.
Plank C, Anton M, Rudolph C, Rosenecker J, Krotz F (2003) Enhancing and targeting nucleic acid delivery by magnetic force. Expert Opin Biol Ther 3:745-758.
Plank C, Schillinger U, Scherer F, Bergemann C, Remy JS, Krotz F, Anton M, Lausier J, Rosenecker J (2003) The magnetofection method: using magnetic force to enhance gene delivery. Biol Chem 384:737-747.
Schwerdt JI, Goya GF, Calatayud MP, Herenu CB, Reggiani PC, Goya RG (2012) Magnetic field-assisted gene delivery: achievements and therapeutic potential. Curr Gene Ther 12:116-126.
Vainauska D, Kozireva S, Karpovs A, Cistjakovs M, Barisevs M (2012) A novel approach for nucleic acid delivery into cancer cells. Medicina (Kaunas) 48:324-329.
Yang SY, Sun JS, Liu CH, Tsuang YH, Chen LT, Hong CY, Yang HC, Horng HE (2008) Ex vivo magnetofection with magnetic nanoparticles: a novel platform for nonviral tissue engineering. Artif Organs 32:195-204.
Yun J, Sonabend AM, Ulasov IV, Kim DH, Rozhkova EA, Novosad V, Dashnaw S, Brown T, Canoll P, Bruce JN, Lesniak MS (2012) A novel adenoviral vector labeled with superparamagnetic iron oxide nanoparticles for real-time tracking of viral delivery. J Clin Neurosci 19:875-880.
Hua Ai et al., Magnetite-Loaded Polymeric Micelles as Ultrasensitive Magnetic-Resonance Probes, Advance Mater, 17, 1949-1952, 2005.
Yuuka Fukui et al., The Preparation of Sugar Polymer-Coated Nanocapsule by the Layer-vy-Layer Deposition on the Liposome, Langmuir; 25(17), 10020-10025, 2009.
D. Cheng, G.B. Hong, W.W. Wang, R.X. Yuan, H, Ai, J. Shen, B.L. Liang, J.M. Gao, X.T. Shuai, Nonclustered magnetite nanoparticle encapsulated biodegradable polymeric micelles with enhanced properties for in vivo tumor imaging; J. Mater. Chem. 21 (2011) 4796-4804.
L.Y.T. Chou, K. Ming, W.C.W. Chan, Strategies for the intracellular delivery of nanoparticles, Chem. Soc. Rev, 40 (2011) 233-245.
T. Dastan, K. Turan, In vitro characterization and delivery of chitosan-DNA microparticles into mammalian cells, J. Pharm. Pharm. Sci. 7 (2004) 205-214.
H. Duan, S. Nie, Cell-penetrating quantum dots based on multivalent and endosomolytic surface coatings, Abstr. Pap. Am. Chem. Soc. 233 (2007).
P. Dutta, S. Pal, M.S. Seehra, N. Shah, G.P. Huffman, Size dependence of magnetic parameters and surface disorder in magnetite nanoparticles, J. Appl. Phys. 105 (2009) 07B501/1-3.

(56) References Cited

OTHER PUBLICATIONS

G.H. Gao, G.H. Im, M.S. Kim, J.W. Lee, J. Yang, H. Jeon, J.H. Lee, D.S. Lee, Magnetite-nanoparticle-encapsulated-pH-responsive polymeric micelle as an MRI probe for detecting acidic pathologic areas, Small 6 (2010) 1201-1204.

H.L. Jiang, J.T. Kwon, E.M. Kim, Y.K. Kim; R. Arote, D. Jere, H.J. Jeong, M.K. Jang, J.W. Nah, C.X. Xu, I.K. Park, M. H. Cho, C.S. Cho, Galactosylated poly(ethylene glycol)-chitosan-graft-polyethylenimine as a gene carrier for hepatocyte-targeting, J. Control. Release 131 (2008) 150-157.

C.W. Jung, P. Jacobs, Physical and chemical-properties of superparamagnetic ironoxide MR contrast agents ferumoxides, ferumoxtran, ferumoxsii, Magn. Reson. Imaging 13 (1995) 661-674.

J.R. Lai, et al., Multifunctional dixorubicin/superparamagnetic iron oxide-encapsulated Pluronic F127 micelles used for chemotherapy/magnetic resonance imaging, J. Appl. Phys 107. (2010).

P.W. Lee, et al., The characteristics, biodistribution, magnetic resonance imaging and biodegradability of superparamagnetic core-shell nanoparticles, Biomaterials 31 (2010) 1316-1324.

E.S. Lee, K. Na, Y.J. Bae, Polymeric micelle for tumor pH and folate-mediated targeting, J. Control. Release 91 (2003) 103-113.

K. Wong, et al., PEI-g-chitosan, a novel gene delivery system with transfection efficiency comparable to polyethylenimine in vitro and after liver administration in vivo, Bioconjug. Chem. 17 (2006) 152-158.

Ragusa, A., et al., Nanoparticles as nonviral gene delivery vectors, IEEE Transactions on Nanobioscience, 2007, vol. 6, No. 4, pp. 319-330.

Basarkar, A., et al., Nanoparticulate systems for the polynucleotide delivery, International Journal of Nanomedicine, 2007, vol. 2, No. 3, pp. 353-360.

Miller, Carin R., Response letter to USPTO Examiner, Response to Non Final Office Action mailed Aug. 26, 2015, U.S. Appl. No. 14/346,330, filed Mar. 21, 2014.

O. Mykhaylyk, et al., Generation of magnetic nonviral gene transfer agents and magnetofection in vitro, Nat6. Protoc. 2 (2007) 2391-2411.

D.L.J. Thorek, et al., Superparamagnetic iron oxide nanoparticles probes for molecular imaging, Ann. Biomed, Eng. 34 (2006) 23-38.

Y.X.J. Wang, et al., Superparamagnetic iron oxide contrast agents: physicochemical characteristics and applications in MR imaging, Eur. Radiol. 11 (2001) 2319-2331.

Miller, Carin R., Response letter to USPTO Examiner, Response to Restriction Requirement in the Office Action of Apr. 17, 2015, U.S. Appl. No. 14/346,330, filed Mar. 21, 2014.

\* cited by examiner

METHODS OF USING MULTILAYER MAGNETIC MICELLE COMPOSITIONS

CROSS REFERENCE TO RELATED APPLICATIONS

This application claims the priority benefit of U.S. Provisional Patent Application Ser. No. 61/602,319 filed Feb. 23, 2012.

STATEMENT REGARDING FEDERALLY SPONSORED RESEARCH OR DEVELOPMENT

This invention was made with Government support under Contract No. N000140810914 awarded by The U.S. Office of Naval Research. The U.S. Government has certain rights in this invention.

BACKGROUND OF THE INVENTION

1) Field of the Invention

The present invention relates to the field of DNA transfection of brain cells.

2) Description of Related Art

Gene therapy is used to treat hereditary diseases such as cystic fibrosis and also acquired diseases such as cancers [M. Conese, et al. Journal of Cystic Fibrosis, 2011, 10, S114], but is only as effective as its ability to deliver the therapeutic polynucleotide to a desired location. Vectors for gene delivery may be viral or nonviral. Viral vectors offer highly efficient gene transfer, but unwanted immune stimulation and the potential for mutagenesis have virtually eliminated them from clinical trials [M. L. Edelstein et al., Journal of Gene Medicine 2007, 9, 833; C. E. Thomas et al., Nature Reviews Genetics 2003, 4, 346]. In contrast, nonviral vectors are safe, have low immunogenicity, and are relatively inexpensive [J. F. Guo et al., Biotechnology Advances 2011, 29, 402].

Examples of nonviral vectors include bacteria [C. H. Chang et al., Biotechnology and Bioengineering 2011, 108], cell penetrating peptides [Y. A. Chen et al., Biomaterials 2011, 32, 4174], functionalized gold nanoparticles or carbon nanotubes [C. M. McIntosh, et al., Journal of the American Chemical Society 2001, 123, 7626; G. Ban et al., Chemical Biology & Drug Design 2006, 67, 78; G. Han et al., Bioconjugate Chemistry 2005, 16, 1356; L. Z. Gao et al., Chembiochem 2006, 7, 239], and cationic polymers. Among these nonviral vectors, cationic polymers including polyethyleneimine (PEI) [U. Lungwitz et al., Eur. J. of Pharmaceutics and Biopharmaceutics 2005, 60, 247], poly(l-lysine) (PLL) [U. Lungwitz et al., Eur. J. of Pharmaceutics and Biopharmaceutics 2005, 60, 247; T. L. Kaneshiro et al., Molecular Pharmaceutics 2007, 4, 759], chitosan [K. Corsi et al., Biomaterials 2003, 24, 1255], dendrimers [J. Dennig, Applications in Materials and Life Sciences 2003, 228, 227; H. M. Wu et al., Biomaterials 2011, 32, 1619] and cationic lipids [M. Morille et al., Biomaterials 2008, 29, 3477] have the advantages of being scalable for manufacturing in quantity and having low immunogenicity, the capacity for selective chemical modification and the ability to carry large inserts. Due to its superior transfection efficiency in a broad range of cell types, synthetic PEI has a privileged place among nonviral gene delivery systems. However, the high number of positive charges on PEI and its lack of biodegradability make it toxic in vivo, which has hampered clinical applications [U. Lungwitz, et al., Eur. J. of Pharmaceutics and Biopharmaceutics 2005, 60, 247; T. L. Kaneshiro et al., Molecular Pharmaceutics 2007, 4, 759].

Chitosan, which is obtained by deacetylation of chitin, is a biocompatible and biodegradable linear polymer whose cationic polyelectrolyte nature provides strong electrostatic interaction with negatively charged DNA to form stable complexes that protect the DNA from degradation. However, the transfection efficiency of chitosan is very low and is dependent on its molecular weight, size and percentage of deacetylation [H. L. Jiang et al. Journal of Controlled Release 2007, 117, 273]. The goal of a successful nonviral gene delivery system, therefore, is to achieve therapeutic efficacy while minimizing toxicity [M. Breunig et al., Proceedings of the National Academy of Sciences of the United States of America 2007, 104, 14454]. To develop such a safe and effective delivery vehicle, PEI-grafted chitosan, chitosan-grafted PEI or a chitosan-PEI composite have been tested and shown to have improved transfection efficiency and reduced toxicity compared to PEI alone [Y. L. Lou et al., Journal of Biomedical Materials Research Part A 2009, 88A, 1058; D. Jere et al., International Journal of Pharmaceutics 2009, 378, 194; H. L, Jiang et al., Gene Therapy 2007, 14, 1389; H. L. Jiang et al., Journal of Biomedical Nanotechnology 2007, 3, 377].

For advanced gene therapy, it is desirable to be able to monitor the in vivo gene delivery in real time. Magnetic resonance imaging (MRI) is a powerful clinical imaging technique for diagnosis of a variety of diseases and post-therapy assessment. MRI contrast can be enhanced by the use of positive or negative contrast agents resulting in brighter (T1-weighted) or darker (T2-weighted) images, respectively. Superparamagnetic iron oxide nanoparticles (SPIONs) are T2 contrast agents that are widely used in molecular and cellular imaging applications [P. Zou et al., Molecular Pharmaceutics 2010, 7, 1974; R. Chen et al., International Journal of Nanomedicine 2011, 6, 511]. Recently, PEI-poly(ethylene glycol) (PEG)-chitosan coated SPIONs have been reported for DNA or siRNA delivery and MRI imaging [F. M. Kievit et al., Advanced Functional Materials 2009, 19, 2244; O. Veiseh et al., Biomaterials 2010, 31] and PEG-grafted PEI-complexed SPION for gene delivery and MRI imaging [G. Chen et al., Biomaterials 2009, 30, 1962]. When incorporated into micelles, a SPION has a longer half-life in circulation and improved biocompatibility, and it shows better contrast. SPION polymeric micelles were used successfully as MRI probes and for drug delivery [N. Nasongkla et al., Nano Letters 2006, 6, 2427; X. T. Shuai et al., Journal of Controlled Release 2004, 98, 41; J. S. Guthi et al., Molecular Pharmaceutics 2010, 7, 32; G. B. Hong et al. Biomedical Microdevices 2008, 10, 693], but they have not been tested for gene delivery.

One area in which gene delivery is particularly difficult is in the targeting of brain tissues. The transport of compounds from the blood to target tissues is restricted by biological barriers such as the blood-brain barrier (BBB). Drug delivery to the brain is particularly hampered because of the tight junctions between adjacent endothelial cells of brain capillaries, which form the BBB. However, some lipid soluble substances can penetrate passively across this barrier, whereas hydrophilic and ionic substances (e.g., amino acids) are transported by a specific carrier transport system.

Efforts have been made to enhance transport via the BBB by conjugating drugs with CNS-permeable moieties. For example, attempts have been made in correcting disorders affecting the CNS system by increasing BBB permeability of exogenous biological compounds such as proteins or specific nucleic acid sequences by conjugating them with lipids. However, none of the prior art approaches provide effective targeting to the brain.

BRIEF DESCRIPTION OF THE DRAWINGS

FIG. 2 also demonstrates that mTBI causes neurodegeneration and the majority of FJ-positive cells are found within the cerebral cortex (FIG. 2B), hippocampus (FIG. 2C) and thalamus (data not shown).

FIG. 4B shows confocal images of sections immunostained with anti SMA antibody showing an intact microvessel in the sham animal and a ruptured microvessel in an area close to the trauma epicenter after mTBI. Scale bar 25 μm. FIG. 4C shows EB florescence and PB staining in cortex and hippocampus after mTBI. Sequential 30 μm coronal sections showing the EB fluorescence and PB staining in the similar regions. Scale bar 100 μm.

FIG. 5A contains representative bright field photomicrographs showing the immunoreactivities. Scale bar 100μ. FIG. 5B provides a histogram showing the integrated density of immunoreactivity measured by image J.* p<0.05, **p<0.001.

DETAILED DESCRIPTION OF THE INVENTION

Figure 1:
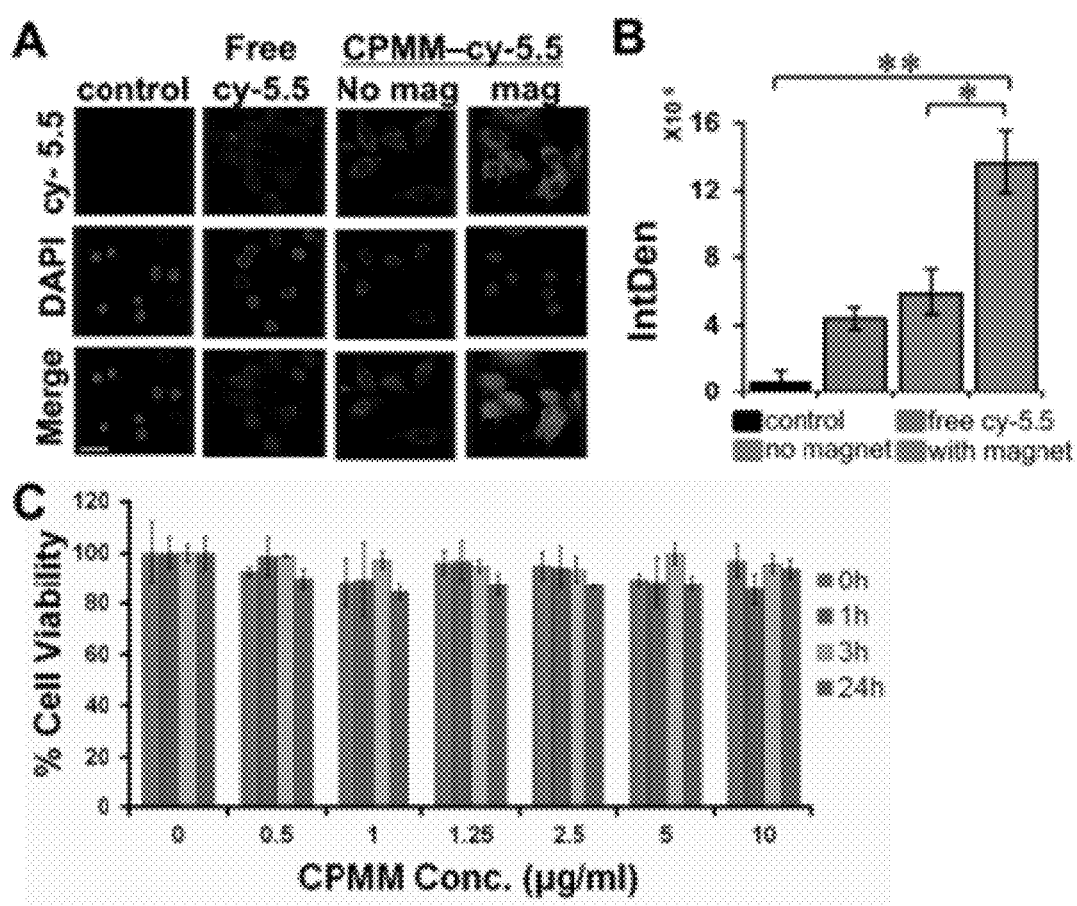
FIG. 1 (A-C) provides confocal microscopic images which show 1) that cells incubated with cy-5.5 conjugated 4MNP nanoparticles with magnet showed significantly higher fluorescence compared to cy-5.5-4MNP without magnet group (FIG. 1A); 2) an integrated density calculation corrected for the background showed highest fluorescence intensity in the cells incubated with cy-5.5—4MNP conjugate with magnet (FIG. 1B); and 3) 4MNP particles at concentrations of 0.5-10 μg/ml and incubated up to 24 hours do not compromise viability of HT22 cells (FIG. 1C).

Provided herein is a method of transfecting a brain cell of a subject comprising systemically administering to the subject a composition comprising a micelle having a hydrophobic superparamagnetic iron oxide nanoparticle (SPION) core, a first coating comprising a cationic polymer, and a second coating comprising a polynucleotide, wherein the subject has a mild traumatic brain injury (TBI). Term definitions used in the specification and claims are as follows:

Definitions

As used in the specification and claims, the singular forms "a," "an" and "the" include plural references unless the context clearly dictates otherwise. For example, the term "a cell" includes a plurality of cells, including mixtures thereof.

The term "active derivative" and the like means a modified chitosan-PEI composition that retains an ability to both protect a polynucleotide and allow for its expression once inside a cell. Assays for testing the ability of an active derivative to perform in this fashion are provided herein.

When referring to a subject or patient, the term "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-peritoneal, intra-synovial, intrasternal, intrathecal, intrahepatic, intralesional, and intracranial injections or infusion techniques. In some embodiments, the administration is intranasal. In other embodiments, the administration is intravenous. As also used herein, the term "systemic administration" refers to an administration that requires the administered composition to cross the blood-brain barrier in order to reach the brain. Accordingly, an intracranial administration is not a systemic administration as that term is used herein.

The term "antibody" is used in the broadest sense and specifically covers monoclonal antibodies (including full-length monoclonal antibodies), polyclonal antibodies, and multispecific antibodies (e.g., bispecific antibodies). Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. Native antibodies and immunoglobulins are usually heterotetrameric glycoproteins of about 150,000 Daltons, composed of two identical light (L) chains and two identical heavy (H) chains. Each heavy chain has at one end a variable domain ($V_H$) followed by a number of constant domains. Each light chain has a variable domain at one end ($V_L$) and a constant domain at its other end. An antibody "specific for" another substance binds, is bound by, or forms a complex with that substance.

The term "antibody fragment" refers to a portion of a full-length antibody, generally the target binding or variable region. Examples of antibody fragments include Fab, Fab', F(ab')$_2$ and Fv fragments. The phrase "functional fragment or analog" of an antibody is a compound having qualitative biological activity in common with a full-length antibody. For example, a functional fragment or analog of an anti-IgE antibody is one which can bind to an IgE immunoglobulin in such a manner so as to prevent or substantially reduce the ability of such a molecule from having the ability to bind to the high affinity receptor, FceRI. As used herein, "functional fragment" with respect to antibodies refers to Fv, F(ab) and F(ab')$_2$ fragments. The Fab fragment contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. F(ab') fragments are produced by cleavage of the disulfide bond at the hinge cysteines of the F(ab')$_2$ pepsin digestion product. Additional chemical couplings of antibody fragments are known to those of ordinary skill in the art. An "Fv" fragment is the minimum antibody fragment which contains a complete target recognition and binding site. This region consists of a dimer of one heavy and one light chain variable domain in a tight, non-covalent association ($V_H$-$V_L$ dimer). It is in this configuration that the three CDRs of each variable domain interact to define a target binding site on the surface of the $V_H$-$V_L$ dimer. Collectively, the six CDRs confer target binding specificity to the antibody. However, even a single variable domain (or half of an Fv comprising only three CDRs specific for a target) has the ability to recognize and bind to a target, although at a lower affinity than the entire binding site. "Single-chain Fv" or "sFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains, which enables the sFv to form the desired structure for target binding.

As used herein, the terms "cancer," "cancer cells," "neoplastic cells," "neoplasia," "tumor," and "tumor cells" (used interchangeably) refer to cells which exhibit relatively autonomous growth so that they exhibit an aberrant growth phenotype characterized by a significant loss of control of cell proliferation (i.e., de-regulated cell division). Neoplastic cells can be malignant or benign. A metastatic cell or tissue means that the cell can invade and destroy neighboring body structures. The cancer can be selected from astrocytoma, adrenocortical carcinoma, appendix cancer, basal cell carcinoma, bile duct cancer, bladder cancer, bone cancer, brain cancer, brain stem glioma, breast cancer, cervical cancer, colon cancer, colorectal cancer, cutaneous T-cell lymphoma, ductal cancer, endometrial cancer, ependymoma, Ewing sarcoma, esophageal cancer, eye cancer, gallbladder cancer, gastric cancer, gastrointestinal cancer, germ cell tumor, glioma, hepatocellular cancer, histiocytosis, Hodgkin lymphoma, hypopharyngeal cancer, intraocular melanoma, Kaposi sarcoma, kidney cancer, laryngeal cancer, leukemia, liver cancer, lung cancer, lymphoma, macroglobulinemia, melanoma, mesothelioma, mouth cancer, multiple myeloma, nasopharyngeal cancer, neuroblastoma, non-Hodgkin lymphoma, osteosarcoma, ovarian cancer, pancreatic cancer, parathyroid cancer, penile cancer, pharyngeal cancer, pituitary cancer, prostate cancer, rectal cancer, renal cell cancer, retinoblastoma, rhabdomyosarcoma, sarcoma, skin cancer, small cell lung cancer, small intestine cancer, squamous cell carcinoma, stomach cancer, T-cell lymphoma, testicular cancer, throat cancer, thymoma, thyroid cancer, trophoblastic tumor, urethral cancer, uterine cancer, uterine sarcoma, vaginal cancer, vulvar cancer and Wilms tumor. In some embodiments, the cancer is prostate cancer.

The terms "cell," "cell line," and "cell culture" include progeny. It is also understood that all progeny may not be precisely identical in DNA content due to deliberate or inadvertent mutations. Variant progeny that have the same function or biological property, as screened for in the originally transformed cell, are included. The "host cells" used in the present invention generally are prokaryotic or eukaryotic hosts.

It should be understood that the term "coating" does not require a complete coverage of the coated object and that partial coverage is encompassed by the term.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

The term "cortex" refers herein to the superficial mantle of gray matter of a subject's brain that covers the cerebral hemispheres and cerebellum. The lateral surface of the human cerebral cortex can be divided into the following regions: lateral occipital, inferior parietal, superior parietal, supra-marginal, pre-central, post-central, superior temporal, middle temporal, inferior temporal, caudal-middle-frontal, pars opercularis, rostral-middle-frontal, and superior frontal. The medial surface of the human cerebral cortex can be divided into the following regions: frontal pole, medial orbito-frontal, superior frontal, paracentral lobule, precuneus, cuneus, peri-calcarine, lingual, fusiform, parahippocampal, entorhinal, isthmus, posterior cingulate, caudal anterior cingulate, rostral anterior cingulate and temporal pole. The hippocampus is an elaboration of the edge of the cerebral cortex.

An "effective amount" is an amount sufficient to effect beneficial or desired results. An effective amount can be administered in one or more administrations, applications, or dosages.

As used herein, "expression" refers to the process by which polynucleotides are transcribed into mRNA and/or the process by which the transcribed mRNA is subsequently translated into peptides, polypeptides, or proteins. If the polynucleotide is derived from genomic DNA, expression may include splicing of the mRNA in a eukaryotic cell. "Overexpression" as applied to a gene refers to the overproduction of the mRNA transcribed from the gene or the protein product encoded by the gene at a level that is 2.5 times higher, preferably 5 times higher, more preferably 10 times higher, than the expression level detected in a control sample.

A "gene" refers to a polynucleotide containing at least one open reading frame that is capable of encoding a particular polypeptide or protein after being transcribed and translated. Any of the polynucleotide sequences described herein may be used to identify larger fragments or full-length coding sequences of the gene with which they are associated. Methods of isolating larger fragment sequences are known to those of skill in the art, some of which are described herein.

A "gene product" refers to the amino acid (e.g., peptide or polypeptide) generated when a gene is transcribed and translated.

"Humanized" forms of non-human (e.g. murine) antibodies are chimeric immunoglobulins, immunoglobulin chains or fragments thereof (such as Fv, Fab, Fab', F(ab')$_2$ or other target-binding subsequences of antibodies) that contain minimal sequence derived from non-human immunoglobulin. In general, the humanized antibody will comprise substantially all of at least one, and typically two, variable domains in which all or substantially all of the CDR regions correspond to those of a non-human immunoglobulin and all or substantially all of the FR regions are those of a human immunoglobulin consensus sequence. The humanized antibody may also comprise at least a portion of an immunoglobulin constant region (Fc), typically that of a human immunoglobulin template chosen.

The term "isolated" means separated from constituents, cellular and otherwise, in which the polynucleotide, peptide, polypeptide, protein, antibody, or fragments thereof are normally associated with in nature. In one aspect of this invention, an isolated polynucleotide is separated from the 3' and 5' contiguous nucleotides with which it is normally associated with in its native or natural environment, e.g., on the chromosome. As is apparent to those of skill in the art, a non-naturally occurring polynucleotide, peptide, polypeptide, protein, or antibody, or fragments thereof, does not require "isolation" to distinguish it from its naturally occurring counterpart. In addition, a "concentrated," "separated," or "diluted" polynucleotide, peptide, polypeptide, protein, or antibody, or fragments thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, or antibody, or fragments thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as glycosylation pattern. Although not explicitly stated for each of the inventions disclosed herein, it is to be understood that all of the above embodiments for each of the compositions disclosed below and under the appropriate conditions are provided by this invention. Thus, a non-naturally occurring polynucleotide is provided as a separate embodiment from the isolated naturally occurring polynucleotide. A protein produced in a bacterial cell is provided as a separate embodiment from the naturally occurring protein isolated from a eukaryotic cell in which it is produced in nature.

As used herein, the term "micelle" refers to an aggregation of molecules wherein hydrophobic portions of the molecules comprise the interior of the aggregation and hydrophilic portions of the molecules comprise the exterior of the aggregation.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single target site. Furthermore, in contrast to conventional (polyclonal) antibody preparations which typically include different antibodies directed against different determinants (epitopes), each monoclonal antibody is directed against a single determinant on the target. In addition to their specificity, monoclonal antibodies are advantageous in that they may be synthesized by the hybridoma culture, uncontaminated by other immunoglobulins. The modifier "monoclonal" indicates the character of the antibody as being obtained from a substantially homogeneous population of antibodies, and it is not to be construed as requiring production of the antibody by any particular method. For example, the monoclonal antibodies for use with the present invention may be isolated from phage antibody libraries using well-known techniques. The parent monoclonal antibodies to be used in accordance with the present invention may be made by the hybridoma method or may be made by recombinant methods.

A "pharmaceutical composition" is intended to include the combination of an active agent with a carrier, inert or active, making the composition suitable for diagnostic or therapeutic use in vitro, in vivo or ex vivo.

The term "pharmaceutically acceptable carrier or excipient" means a carrier or excipient that is useful in preparing a pharmaceutical composition that is generally safe, non-toxic and neither biologically nor otherwise undesirable and includes a carrier or excipient that is acceptable for veterinary use as well as human pharmaceutical use. A "pharmaceutically acceptable carrier or excipient" as used in the specification and claims includes both one and more than one such carrier or excipient. As used herein, the term "pharmaceutically acceptable carrier" encompasses any of the standard pharmaceutical carriers, such as a phosphate buffered saline solution, water, emulsions, such as an oil/water or water/oil emulsion, and various types of wetting agents. The compositions also can include stabilizers and preservatives.

The term "pharmaceutically acceptable salts" refers to any acid or base addition salt whose counter-ions are non-toxic to the subject to which they are administered in pharmaceutical doses of the salts. Specific examples of pharmaceutically acceptable salts are provided below.

The terms "pharmaceutically effective amount," "therapeutically effective amount," or "therapeutically effective dose" refer to the amount of a compound that will elicit the biological or medical response of a tissue, system, animal, or human that is being sought by the researcher, veterinarian, medical doctor or other clinician.

The term "therapeutically effective amount" includes that amount of a compound that, when administered, is sufficient to prevent development of, or alleviate to some extent one or more of the symptoms of, the condition or disorder being treated. The therapeutically effective amount will vary depending on the compound, the disorder or conditions and their severity, the route of administration, time of administration, rate of excretion, drug combination, judgment of the treating physician, dosage form, and the age, weight, general health, sex and/or diet of the subject to be treated.

The term "traumatic brain injury," or TBI, refers to an injury of a subject's brain that is caused by an external force. Causes of TBI include, but are not limited to, falls, vehicle accidents and violence. TBI is classified as mild, moderate, or severe. Any classification system or method known to those of skill in the art can be used to classify TBI. In one embodiment, TBI is classified using the Glasgow Coma Scale (GCS). The GCS grades a subject's level of consciousness on a scale of 3-15 based on verbal, motor, and eye-opening reactions to stimuli. A GCS of 13 or above is mild TBI, 9-12 is moderate TBI, and 8 or below is severe TBI. Mild TBI can also be classified as an injury from which a subject suffers post-traumatic amnesia for less than one day and/or suffers from a loss of consciousness for 0-30 minutes. In some embodiments, mild TBI is considered a concussion, which concussion can be mild, moderate or severe.

The terms "polynucleotide" and "oligonucleotide" are used interchangeably and refer to a polymeric form of nucleotides of any length, either deoxyribonucleotides or ribonucleotides, or analogs thereof. Polynucleotides may have any three-dimensional structure and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, polynucleotide probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine (T) when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "polypeptide" is used in its broadest sense to refer to a compound of two or more subunit amino acids, amino acid analogs, or peptidomimetics. The subunits may be linked by peptide bonds. In another embodiment, the subunit may be linked by other bonds, e.g., ester, ether, etc. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

"Selectively binds" refers to a non-specific binding event as determined by an appropriate comparative control. Binding is selective when the binding is at least 10, 30, or 40 times greater than that of background binding in the comparative control.

A "subject," "individual," or "patient," used interchangeably herein, refers to a vertebrate, preferably a mammal, more preferably a human. Mammals include, but are not limited to, murines, simians, humans, farm animals, sport animals, and pets.

"Transformation" of a cellular organism with DNA means introducing DNA into an organism so that the DNA is replicable, either as an extrachromosomal element or by chromosomal integration. "Transfection" of a cellular organism with DNA refers to the taking up of DNA, e.g., an expression vector, by the cell or organism whether or not any coding sequences are in fact expressed. The terms "transfected host cell" and "transformed" refer to a cell in which DNA was introduced. The cell is termed "host cell" and it may be either prokaryotic or eukaryotic. Typical prokaryotic host cells include various strains of E. coli. Typical eukaryotic host cells are mammalian, such as Chinese hamster ovary or cells of human origin. The introduced DNA sequence may be from the same species as the host cell or from a different species than the host cell, or it may be a hybrid DNA sequence, containing some foreign and some homologous DNA.

The term "vector" means a DNA construct containing a DNA sequence which is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites, and sequences which control the termination of transcription and translation. The vector may be a plasmid, a phage particle, or simply a potential genomic insert. Once transformed into a suitable host, the vector may replicate and function independently of the host genome or may, in some instances, integrate into the genome itself. In the present specification, "plasmid" and "vector" are sometimes used interchangeably, as the plasmid is the most commonly used form of vector. However, the invention is intended to include such other forms of vectors which serve equivalent functions as those in the art and which are, or become known, in the art.

As discussed above, provided herein is a method of transfecting a brain cell of a subject with a polynucleotide comprising systemically administering to the subject a composition comprising a micelle having a hydrophobic superparamagnetic iron oxide nanoparticle (SPION) core, a first coating comprising a cationic polymer, and a second coating comprising the polynucleotide, wherein the subject has a mild traumatic brain injury (TBI). In some embodiments, the brain cell is further transformed with the polynucleotide.

In one embodiment, TBI is classified using the Glasgow Coma Scale (GCS). The GCS grades a subject's level of consciousness on a scale of 3-15 based on verbal, motor, and eye-opening reactions to stimuli. A GCS of 13 or above is mild TBI, 9-12 is moderate TBI, and 8 or below is severe TBI. In another or further embodiment, TBI is classified as an injury from which a subject suffers post-traumatic amnesia for less than one day or a loss of consciousness for 0-30 minutes and/or from which a subject's level of consciousness is rated 13 or above on a GCS scale. In some embodiments, mild TBI is considered a concussion, which concussion can be mild, moderate, or severe.

The compositions administered according to the present invention comprise a micelle having a superparamagnetic iron oxide nanoparticle (SPION) core, a first coating comprising one or more cationic polymers and a second coating comprising a polynucleotide. Some embodiments of this composition are referred to herein as 4MNPs. In one embodiment, the 4MNPs were prepared and conjugated with DNA as described by Wang et al. [C. Wang et al., Journal of Controlled Release 2012, 163, 82]. mPEG-PLA-OH diblock copolymers were synthesized from DL-dilactide and methoxypolyethylene glycol (mPEG) of various molecular weights using stannous 2-ethyl-hexanoate as a catalyst by catalyzed ring-opening polymerization [A. Lucke et al., Biomaterials, 2000, 21, 2361]. First, the DL-dilactide was vacuum-dried at room temperature for 4 hours and the mPEG was vacuum-dried at 80° C. for 3 hours. Then the dried mPEG, a specific amount of dry DL-dilactide, the stannous 2-ethyl-hexanoate (3% w/w) and 20 mL of toluene were added into a two-neck flask and mixed. The reaction solution was refluxed for 5 hours at 140° C. under argon gas protection and precipitated with cold diethyl ether. The purified product was kept under vacuum at room temperature for 24 hours. SPIONs were prepared according to the procedure of Sun et al. [S. Sun & H. Zeng, Journal of the American Chemical Society, 2002, 124, 8204]. The black SPION product was dissolved in dichloromethane in the presence of oleic acid (0.05 ml) and oleylamine (0.05 ml). CS-mag micelles were prepared by the solvent evaporation method. Dichloromethane solutions of 500 µl of 25 µg/µl mPEG-PLA and 300 µl of 4 mg/ml SPIONs were added drop-wise to 10 ml of a 10 mg/ml solution of water-soluble chitosan (10 kDa, degree of deacetylation 85%, donated by Transgenex NanoBioTech, Inc. Tampa) with vigorous stirring. The $CH_2Cl_2$ was allowed to evaporate slowly at ambient conditions overnight. The micelle solution was filtered through a 0.2 µm nylon membrane filter and freeze-dried. Chitosan-PEI-mag-micelles (4MNPs) were prepared in a weight ratio of chitosan to PEI of 1:1. CS-mag-micelle solution in water (2 mg/ml) was mixed with PEI (2 mg/ml) at a v/v ratio of 1:1 with stirring and was refrigerated for storing.

The cationic polymers found in the first coating of the 4MNPs include, but are not limited to, chitosan, polyethyleneimine (PEI), poly(l-lysine) (PLL), dendrimers, and cationic lipids. In some embodiments, the first coating comprises chitosan, wherein chitosan has a chemical formula of:

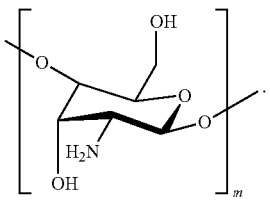

I wherein m is between 1 and 10,000, or an active derivative thereof. Also included herein are compositions comprising chitosan having Formula I wherein m is between 1 and 5,000, 1 and 2,000, 1 and 1,000, 1 and 500, 1 and 200, 1 and 50, 50 and 70, or 1 and 20. Further included herein are compositions comprising chitosan having Formula I wherein m is approximately 60. Chitosan is a linear polysaccharide composed of randomly distributed β-(1-4)-linked D-glucosamine (deacetylated unit) and N-acetyl-D-glucosamine (acetylated unit). On average, the molecular weight of commercially produced chitosan is between 3,800 and 20,000 Daltons. In some embodiments, the first coating is prepared with a chitosan having a molecular weight of approximately 3-12 kDa. In one embodiment, the chitosan is water soluble and has a molecular weight of approximately 10 kDa.

In other or further embodiments, the first coating comprises PEI, wherein PEI has a chemical formula of:

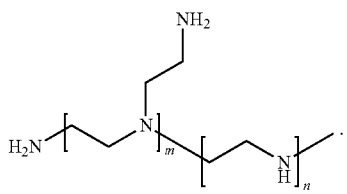

II wherein m is between 1 and 10,000, and n is between 1 and 10,000, or an active derivative thereof. Also included herein are PEI compounds wherein m or n is between 1 and 5,000, 1 and 2,000, 1 and 1,000, 1 and 500, 1 and 200, 1 and 50, or 1 and 20. In some embodiments, the PEI is a branched PEI having a molecular weight of approximately 25 kDa. In some embodiments, the PEI is a linear PEI having a molecular weight of approximately 25 kDa.

The chitosan, PEI, and polynucleotide can be in any amount. However, in some embodiments, the polynucleotide is at a concentration between approximately 1 and 3 μg/ml (including approximately 1 μg/ml, 2 μg/ml and 3 μg/ml). In further or other embodiments, the molar weight ratio of chitosan and the polynucleotide is between approximately 3:1 and 7:1. In still further or other embodiments, the molar weight ratio of PEI and the polynucleotide is between approximately 7:1 and 3:1. In yet further or other embodiments, the molar weight ratio of chitosan and PEI is between approximately 3:7 and 7:3. Accordingly, provided herein are compositions for administration comprising a micelle having a superparamagnetic iron oxide nanoparticle (SPION) core, a first coating comprising chitosan and PEI, and a second coating comprising a polynucleotide, wherein the chitosan/PEI/polynucleotide molar weight ratio is between approximately 3:3:1 and 7:7:1 and includes chitosan/PEI/polynucleotide molar weight ratios of approximately 3:7:1, 7:3:1, and 5:5:1.

Accordingly, in some embodiments the composition for administration comprises a micelle having a superparamagnetic iron oxide nanoparticle (SPION) core, a first coating comprising chitosan having the chemical formula of I and PEI having the chemical formula of II, and a second coating comprising a polynucleotide. In one embodiment, the composition comprises a micelle having a superparamagnetic iron oxide nanoparticle (SPION) core, a first coating comprising chitosan having the chemical formula of I wherein m is between approximately 1 and 10,000, and PEI having the chemical formula of II wherein m is between approximately 1 and 10,000 and n is between approximately 1 and 10,000, and a second coating comprising a polynucleotide. In a further embodiment, the composition comprises a micelle having a superparamagnetic iron oxide nanoparticle (SPION) core, a first coating comprising chitosan having the chemical formula of I and a molecular weight of approximately 10 kDa, and PEI having the chemical formula of II and a molecular weight of approximately 25 kDa, and a second coating comprising a polynucleotide.

The term micelle is used herein to refer to an aggregation of molecules wherein hydrophilic portions of the molecules comprise the interior of the aggregation and hydrophobic portions of the molecules comprise the exterior of the aggregation. In some embodiments the molecules that comprise the micelle are copolymers of polyethylene glycol and poly D, L-dilactide. In certain further embodiments, the molecules that comprise the micelle have the chemical formula of III:

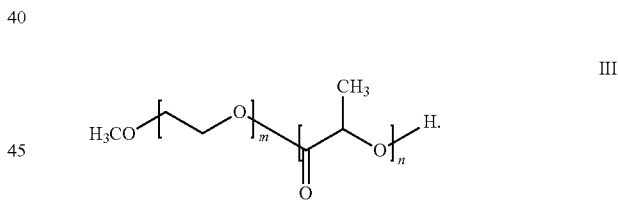

III wherein m is between 1 and 10,000, n is between 1 and 10,000, or an active derivative thereof. Also included herein are copolymers of polyethylene glycol and poly D, L-dilactide wherein m or n is between 1 and 5,000, 1 and 2,000, 1 and 1,000, 1 and 500, 1 and 200, 1 and 50, or 1 and 20. In one embodiment, the copolymer is prepared using a polyethylene glycol that is a monomethoxy glycol (mPEG) having a molecular weight of approximately 20 kDa. In another or further embodiment, the copolymer of polyethylene glycol and poly D, L-dilactide has a molecular weight between 10 and 30 kDa.

At the center or core of the micelle structure provided herein is a superparamagnetic iron oxide nanoparticle (SPION). In some embodiments, the SPION is hydrophobic. In some embodiments, the SPION core comprises a coating of oleic acid and oleylamine. The SPION can be prepared by any method known to those of skill in the art. In one embodiment, the SPION is prepared using iron, 1,2-dodecanediol, oleic acid, oleylamine, and benzyl ether.

The compositions provided herein comprise a micelle having a superparamagnetic iron oxide nanoparticle (SPION) core, a first coating comprising one or more cationic polymers, and a second coating comprising a polynucleotide. In some embodiments, these compositions further comprise a ligand. A ligand is defined herein as any moiety that facilitates binding of the compositions provided herein to a target such as a cell. Ligands include, but are not limited to, antibodies, adhesion molecules, lectins, integrins, and selectins. When the ligand is an antibody, it can comprise approximately 1% of the total composition weight (but is not limited to such amount).

The composition described herein can be administered systemically via any route known to those of skill in the art. A "systemic administration" refers herein to an administration that requires the administered composition to cross the blood-brain barrier in order to reach the brain. In one embodiment, a 4MNP composition is administered intranasally. It should be understood that the compositions described herein can be administered at any time following a traumatic brain injury. In some embodiments, the compositions are administered to a subject approximately 1-5 hours, 1-10 hours, 1-18 hours, 1-24 hours, 1-36 hours, or 1-48 hours following the occurrence or commencement of a mild traumatic brain injury.

As the examples below further demonstrate, administering 4MNP nanoparticles comprising a pCMV-td Tomato plasmid encoding the Tomato-red fluorescent protein (RFP) to the brains of rats resulted in moderate transfection in the cortex and hippocampus after mTBI as measured by the integrated density of the RFP immunofluorescence. Iron oxide from the nanoparticles, as well as red-fluorescent protein, was observed in different areas of the cortex and the hippocampus in close proximity to degenerating neurons. This is important because specific expression of the reporter protein in brain cells of mTBI rats demonstrates that the 4MNP particles could be used to carry therapeutic DNA to injured areas of the brain. Expression of the Tomato-red fluorescent gene was observed 48 hours after mTBI and intranasal administration of 4MNP-td Tomato plasmid complex. It indicates that the td Tomato plasmid DNA was released at a slow rate and that the time of reporter gene expression coincides with the time of inflammatory gene expression as observed previously in similar brain regions and under similar experimental conditions [M. Das et al., Journal of Neuroinflammation 2011, 8, 148]. This indicates the potential of gene therapy using 4MNP nanoparticles to minimize pro-inflammatory chemokine production in the brain after TBI and thereby reduce neurodegeneration.

The main challenge of gene delivery to the brain is the blood-brain barrier (BBB). Some relatively small nanoparticles (about 35 nm) are able to cross the BBB, but loading the 4MNPs with DNA as described herein increased the size of the nanoparticles to around 290 nm, which hindered their delivery across the BBB (as observed in the naïve and sham animals in this study). Following mTBI, the BBB is transiently compromised, and during that period, molecules of different sizes can enter the brain tissues. That time window was utilized for intranasal administration of 4MNP-td Tomato plasmid complexes in order to evaluate the efficacy of these particles to deliver the reporter gene into cells in the damaged tissues. It was observed that in this model of mTBI, the BBB remains open at least until 24 hours post-injury. This suggests a therapeutic time window for gene/drug delivery after mTBI.

These studies, which used biocompatible 4MNP-td Tomato plasmid conjugates given to rats sham-operated or subjected to mTBI, showed that the 4MNP-td Tomato plasmid conjugates are an excellent DNA carrier that release DNA slowly over a period of 48 hours in the cells. It is expected that these nanoparticles can be used for gene therapy to prevent the secondary neurodegeneration following mTBI. Also, these nanoparticles are non-immunogenic as observed in this study.

Additionally, the SPIONs incorporated into the 4MNPs would allow real-time monitoring of the gene delivery into the brain. The ability to be cleared relatively rapidly, the nontoxic nature of these particles, and their MRI contrast property make them an ideal candidate for gene therapy in cases of mild brain injury. Moreover, the SPION core allows the nanoparticles to be condensed in the brain under magnetic field and thereby make the delivery of a larger payload of DNA to the tissue possible.

It should be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims. All patents, patent applications, and publications referenced herein are incorporated by reference in their entirety for all purposes.

EXAMPLES

Example 1

Preparation of Multilayered Mag-Micelles (4MNPs)

The 4MNPs were prepared and conjugated with DNA as described by Wang et al. [C. Wang et al., Journal of Controlled Release 2012, 163, 82], mPEG-PLA-OH diblock copolymers were synthesized from DL-dilactide and methoxypolyethylene glycol (mPEG) of various molecular weights using stannous 2-ethyl-hexanoate as a catalyst by catalyzed ring-opening polymerization [A. Lucke et al. Biomaterials 2000, 21, 2361]. First, DL-dilactide was vacuum-dried at room temperature for 4 hours and mPEG (MW 20 K Da) was vacuum-dried at 80° C. for 3 hours. Then 0.5 g of dried mPEG, 3 g of dry DL-dilactide, the stannous 2-ethyl-hexanoate (3% w/w) and 20 mL of toluene were added into a two-neck flask and mixed. The reaction solution was refluxed for 5 hours at 140° C. under argon gas protection and precipitated with cold diethyl ether. The purified product was kept under vacuum at room temperature for 24 hours. SPIONs were prepared according to the procedure of Sun et al. [S. Sun & H. Zeng, Journal of the American Chemical Society 2002, 124, 8204]. The black SPION product was dissolved in dichloromethane in the presence of oleic acid (0.05 ml) and oleylamine (0.05 ml). CS-mag micelles were prepared by the solvent evaporation method. Dichloromethane solutions of 500 µl of 25 µg/µl mPEG-PLA and 300 µl of 4 mg/ml SPIONs were added drop-wise to 10 ml of a 10 mg/ml solution of water-soluble chitosan (10 kDa, degree of deacetylation 85%, donated by Transgenex NanoBioTech, Inc. Tampa) with vigorous stirring. The $CH_2Cl_2$ was allowed to evaporate slowly at ambient conditions overnight. The micelle solution was filtered through a 0.2 µm nylon membrane filter and freeze-dried.

Chitosan-PEI-mag-micelles (4MNPs) were prepared in a weight ratio of chitosan to PEI 1:1. CS-mag-micelle solution in water (2 mg/ml) was mixed with PEI (2 mg/ml) at a v/v ratio of 1:1 with stirring and refrigerated for storing.

Example 2

Cellular Uptake of 4MNP and its Effect On Cell Viability

HT22 cells were treated with free cy-5.5 dye or cy-5.5 conjugated 4MNP with or without magnet for 1 hour. HT22 cells (donated by Dr. Bruce Citron, Bay Pine VA Hospital, Fla.) were cultured in DMEM with 10% FBS and 1% penicillin/streptomycin in an atmosphere of 5% $CO_2$. Cells were plated at a density of 20,000 per well in 8 well-chamber slides 24 hours prior to the experiment. cy-5.5 was conjugated to the 4MNP nanoparticles at a ratio of 4MNP:cy-5.5 of 1:10 and dialyzed for 24 hours to remove excess cy-5.5. 4MNP-cy-5.5 conjugate equivalent to 2.5 µg/ml 4MNP was added to the cells and incubated at 37° C. for 1 hour with or without a bar magnet underneath the wells. An equal amount of free cy-5.5 was used as a control. After 1 hour, cells were washed 3 times with sterile PBS and fixed with 4% paraformaldehyde for 10 minutes, washed with sterile PBS and cover slipped using DAPI containing mounting medium. Cells were observed using a Leica TCS SP2 laser scanning confocal microscope and photos were taken.

All data are presented as mean±S.E.M. Statistical significance was evaluated by one-way ANOVA with Bonferroni's post-hoc test. A p-value of less than 0.05 was considered statistically significant for all comparisons.

Confocal microscopic images show cy-5.5 fluorescence after 1 hour in all three groups but free cy-5.5 showed least fluorescence. On the other hand, cells incubated with cy-5.5 conjugated 4MNP nanoparticles with magnet showed significantly higher fluorescence compared to cy-5.5-4MNP without-magnet group (FIG. 1A). Integrated density calculation, corrected for the background, showed highest fluorescence intensity in the cells incubated with cy-5.5—4MNP conjugate with magnet (FIG. 1B).

The cytotoxic effect of the 4MNP nanoparticles was also tested on HT22 cells. HT22 cell viability was measured using a WST assay kit (Roche Applied Science, Indianapolis, Ind.). Cells at 80% confluence were trypsinized and seeded in a 96-well plate at a density of 3500 cells/well. At 24 hours after plating, the cells were treated with different concentrations of 4MNP in a final volume of 100 µL per well and incubated for 1 hour, 3 hours, and 24 hours at 37° C. with 5% $CO_2$. During incubation, the wells were placed on a magnet for the first hour. WST reagent was added following the manufacturer's instructions, and after 4 hours, the plate was read at 540 nm and 630 nm using a Synergy H4 microplate reader. Cell viability was calculated using the formula:

Cell Viability (%)=100×(OD sample/OD control)

Results from WST assays (FIG. 1C) show that these particles at concentrations of 0.5-10 µg/ml and incubated up to 24 hours do not compromise viability of HT22 cells. At these concentrations, cells show healthy growth and normal cellular architecture even after 24 hours of treatment. Accordingly, these studies demonstrate that 4MNP nanoparticles were not toxic to the neuronal cell line HT22 even after 24 hours. Neurons are difficult to transfect, yet these nanoparticles were readily taken up by HT22 cells.

Example 3

Effect of Magnetic Field on the Concentration of 4MNP in the Brain after Mild TBI To observe whether magnetofection causes any differences in concentrating 4MNP nanoparticles in the brain or not, rats were subjected to mild TBI (mTBI) to the cerebral cortex or were sham operated and, immediately thereafter, td Tomato plasmid-complexed 4MNPs were administered intranasally (i.n.). One group of 6 rats, including 3 sham and 3 mTBI animals, were subjected to a magnetic field for 1 hour. Another group of 6 rats, also including 3 sham and 3 mTBI animals, were not. The degree of Prussian Blue (PB) staining was compared between the two groups.

All animal procedures were conducted in accordance with the NIH Guide for the Care and Use of Laboratory Animals following a protocol approved by the Institutional Animal Care and Use Committee at the University of South Florida. Male Sprague-Dawley rats (Harlan, Indianapolis, Ind.) weighing 250 to 300 g were housed in a climate-controlled room with 12/12 hour day-night cycle, water and laboratory chow available ad libitum. A total of 33 animals were used in this study.

Brain trauma was induced in rats via a lateral fluid percussion injury (LFPI) device as described previously [M. Das et al., Journal of Neuroinflammation 2011, 8, 148]. Animals were anesthetized with ketamine (90 mg/kg)/xylazine (10 mg/kg) (IP) and a 1 mm diameter craniotomy was performed centered at 2 mm lateral and 2.3 mm caudal to the bregma on the right side of the midline. A female luer-lock hub was implanted at the craniotomy site, secured with dental cement and attached via tubing to the FPI device. A mild impact ranging from 2.0-2.2 atm was administered S. V. Kabadi, Nature Protocols, 2010, 5, 1552]. The hub was then detached, the craniotomy hole was sealed with bone wax and the scalp was sutured. Ketoprofen (5 mg/kg) was administered to minimize postsurgical pain and discomfort. Rats were then replaced in their home cages and allowed to recover for 48 hours prior to euthanasia. Animals were excluded from the experiment if the impact did not register between 2.0 and 2.2 atm or if the dura was disturbed during the craniotomy. In sham (control) animals, craniotomy was performed at the same coordinates as the TBI animals but no impact was delivered.

The Prussian Blue staining was performed as follows: Freshly prepared 5% potassium ferrocyanide ($K_4Fe(CN)_6$) solution and 5M HCl were mixed in a ratio of 1:1 (v/v). Slide mounted sections were washed in PBS and incubated in ferrocyanide solution in a Coplin jar for 72 hours. The slides were then washed in DI water and counterstained with eosin, dehydrated with graded alcohols, cleared with xylene and mounted with Vectamount mounting medium.

Figure 2:
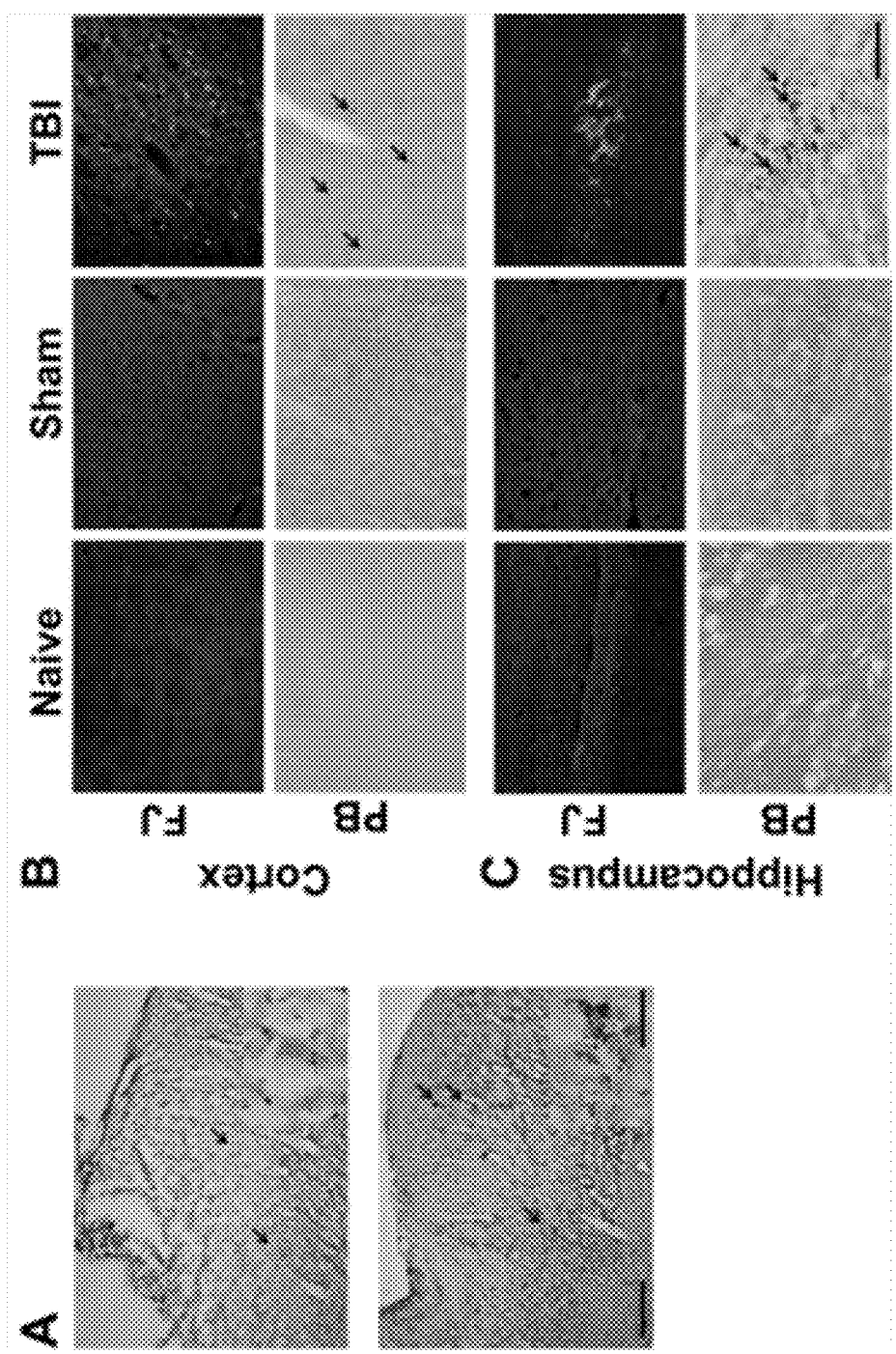
FIG. 2 (A-C) shows the results of Prussian Blue staining which indicate that more 4MNPs were concentrated in the cortex of the rats subjected to magnetic field (FIG. 2A upper image) compared to the other group recovered without magnet (FIG. 2A lower image).

PB staining revealed that more 4MNPs were concentrated in the cortex of the rats subjected to magnetic field (FIG. 2A upper image) compared to the other group recovered without magnet (FIG. 2A lower image). All subsequent experiments were performed by subjecting the rats under the same magnetic field following sham or mTBI and i.n. 4MNP administration.

Following mTBI, the pattern and extent of neurodegeneration observed in these experiments are in accordance with those reported previously [M. Das et al., Journal of Neuroinflammation 2011, 8, 148]. mTBI causes neurodegeneration and the majority of FJ-positive cells are found within the cerebral cortex (FIG. 2B), hippocampus (FIG. 2C) and thalamus (data not shown). Degenerating cortical neurons were observed around the epicenter of the trauma and on the lateral cortex. Hippocampal neurodegeneration was localized to the pyramidal cell layers with some diffuse labeling throughout the general structure. PB staining of matching sections shows the presence of iron oxide nanoparticles in the cortex and hippocampus even 48 hours after mTBI followed by i.n. administration of 4MNP (FIGS. 2B and 2C, lower panels). Also, most of the particles were found on the side of the brain ipsilateral to the injury. No PB staining was observed in the thalamus. Both FJ and PB staining was absent in sham animals.

Example 4

Transfection of Rat Brain Cells with 4MNP-Associated DNA

Adult male SD rats were subjected to mild traumatic brain injury (mTBI using a lateral fluid percussion injury device or a sham operation. 4MNP-DNA (td Tomato plasmid) complexes were delivered intranasally immediately after mTBI or sham surgery.

The pCMV-td Tomato plasmid (Clontech) encoding the Tomato-red fluorescent protein (RFP) was extracted and purified using the MegaPrep plasmid purification kit (Qiagen) from a culture of XL1-Blue cells transformed with the plasmid. 4MNPs (0.2 μg/μl, 10 kD) and plasmid DNA (0.2 μg/μl) in phosphate-buffered saline (PBS, pH 7.4) were prepared separately. The plasmid DNA solution was added drop-wise to 4MNP solution and vortexed for 20 minutes. The 4MNP-DNA conjugate was instilled into the nostrils of anesthetized rats at 50 μl per nostril immediately after mTBI or sham surgery. The rats were then placed on a 37° C. heating pad in their home cage with or without a magnetic cap on the head for 1 hour and allowed to recover. Euthanasia was performed at 24 or 48 hours.

Red-fluourescent protein (RFP) immunohistochemistry was performed as follows: Slide-mounted tissue sections were washed with PBS and pretreated for immunohistochemistry as described. The sections were permeabilized in 10% goat serum, 0.1% Triton X-100 in PBS for 1 hour and incubated overnight at 4° C. with rabbit anti-DsRed primary antibody (1:1000) (Abcam, Cambridge, Mass.) in antibody solution (5% goat serum, 0.05% Triton X-100 in PBS). The next day, the sections were washed with PBS and incubated for 1 hour at room temperature with biotinylated goat anti-rabbit antibody, 1:400, (Vector Laboratories Inc., Burlingame, Calif.) in antibody solution. Sections were then washed in PBS and incubated with DyLight 594-conjugated anti-rabbit antibody (1:200) for 1 hour at room temperature, washed with PBS, dried and cover slipped with Vectashield aqueous mounting medium with DAPI.

All quantitation was performed using the NIH image J software. For immunohistochemical analysis, images were acquired using an Olympus IX71 microscope controlled by DP70 manager software (Olympus America Inc., Melville, N.Y.). Photomicrographs captured at 200× magnification with an Olympus DP70 camera were used for quantitation. Images were taken at the same exposure and digital gain settings for a given magnification to minimize differential background intensity or false-positive immunoreactivity across sections. The channels of the RGB images were converted to gray-scale before quantitation. The gray-scale images were then adjusted for brightness and contrast to exclude noise pixels. The images were also adjusted for the threshold to highlight all the positive cells to be counted and a binary version of the image was created with pixel intensities between 0 and 255. Integrated density (IntDen) was calculated and background correction was performed for each image. The corrected integrated density of immunoreactivity of the sections from 1.5, 2.5 and 3.5 mm caudal to the bregma were averaged to represent the IntDen of immunoreactivity from each brain and expressed as mean IntDen±S.E.M.

Fluoro-Jade (FJ) (Histochem, Jefferson, Ark.) staining was performed to label degenerating neurons. This method was adapted from that originally developed by Schmued et al. [L. C. Schmued et al., Brain Research 1997, 751, 37] and subsequently detailed by Duckworth [E. A. Duckworth et al., Brain Research 2005, 1042, 29]. Thaw-mounted sections were placed in 100% ethanol for 3 minutes followed by 70% ethanol and deionized (DI) water for 1 minute each. Sections were then oxidized with 0.06% $KMnO_4$ solution for 15 minutes followed by three rinses in DI water for 1 minute each. Sections were then stained in a 0.001% solution of Fluoro-Jade in 0.1% acetic acid for 30 minutes. Slides were rinsed, dried at 45° C. for 20 minutes, cleared with xylene, and cover-slipped using DPX mounting medium (Electron Microscopy Sciences, Ft. Washington, Pa.).

Figure 3A:
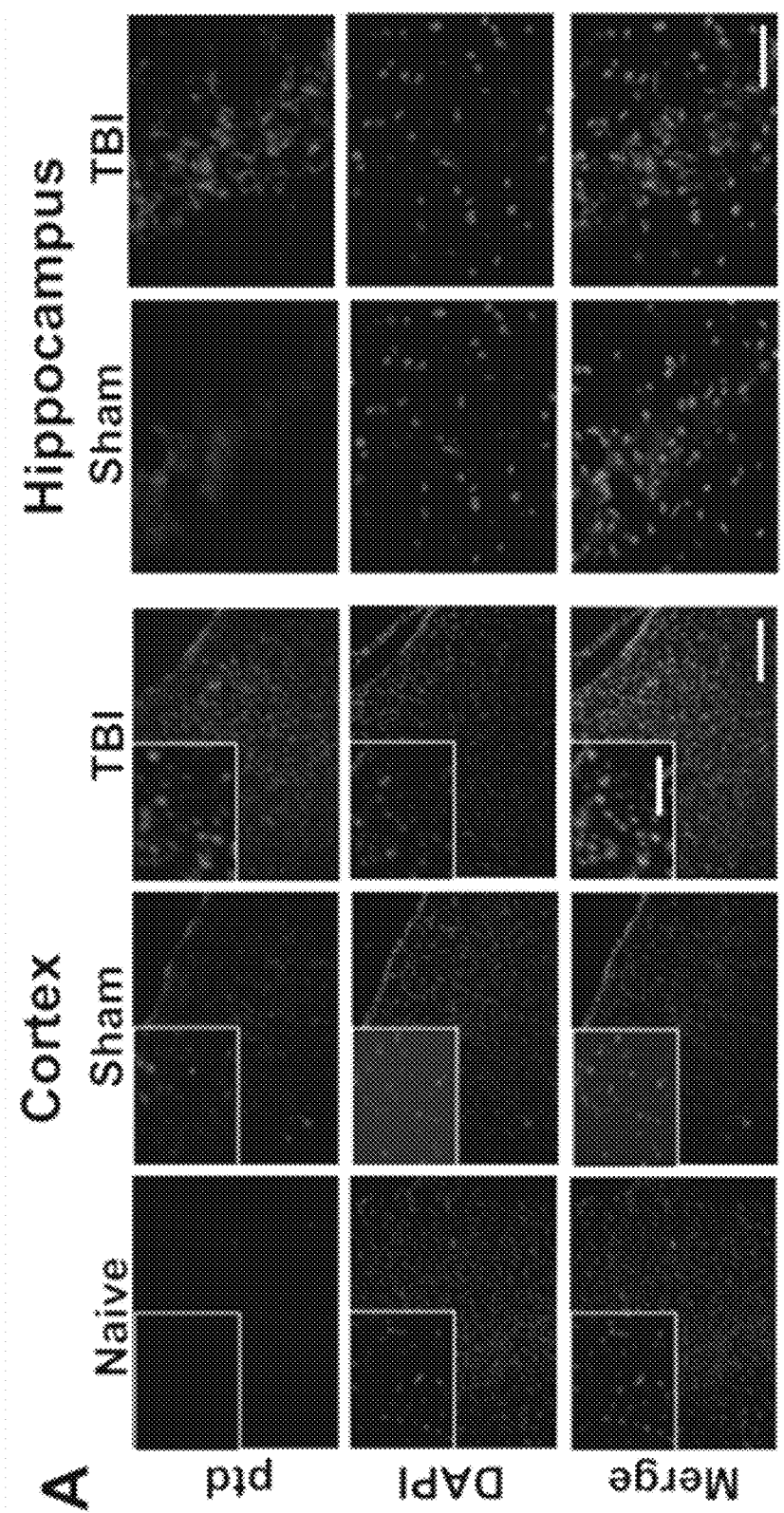
FIG. 3 (A-C) shows that animals with mTBI showed substantial red fluorescent protein (RFP) expression in the cortex and hippocampus (FIG. 3A). The upper panels of FIG. 3B show the results of PB staining performed on lung, liver, kidney and spleen sections to determine if 4MNP nanoparticles were present in those organs. The lower panels of FIG. 3B show that no RFP expression was observed in spleen and kidney.
FIG. 3C shows there was not much difference between sham and mTBI animals with regard to RFP expression in lung and liver.

Naïve rats received no nanoparticles or surgery and no RFP expression was observed in their brain tissues. A few RFP-positive cells were found in the cortex of sham animals. On the other hand, animals with mTBI showed substantial RFP expression in the cortex and hippocampus (FIG. 3A). Most expression in the cortex was observed in the tissues around the trauma epicenter and in the lateral cortex where most of the FJ-positive cells were observed, although other areas of the cortex also had cells expressing REP. In the hippocampus the td Tomato plasmid expression was observed in the pyramidal cell layer and also in the general structure of the hippocampus.

Example 5

Biodistribution of 4MNP and RFP Expression Following mTBI

Figure 3B:
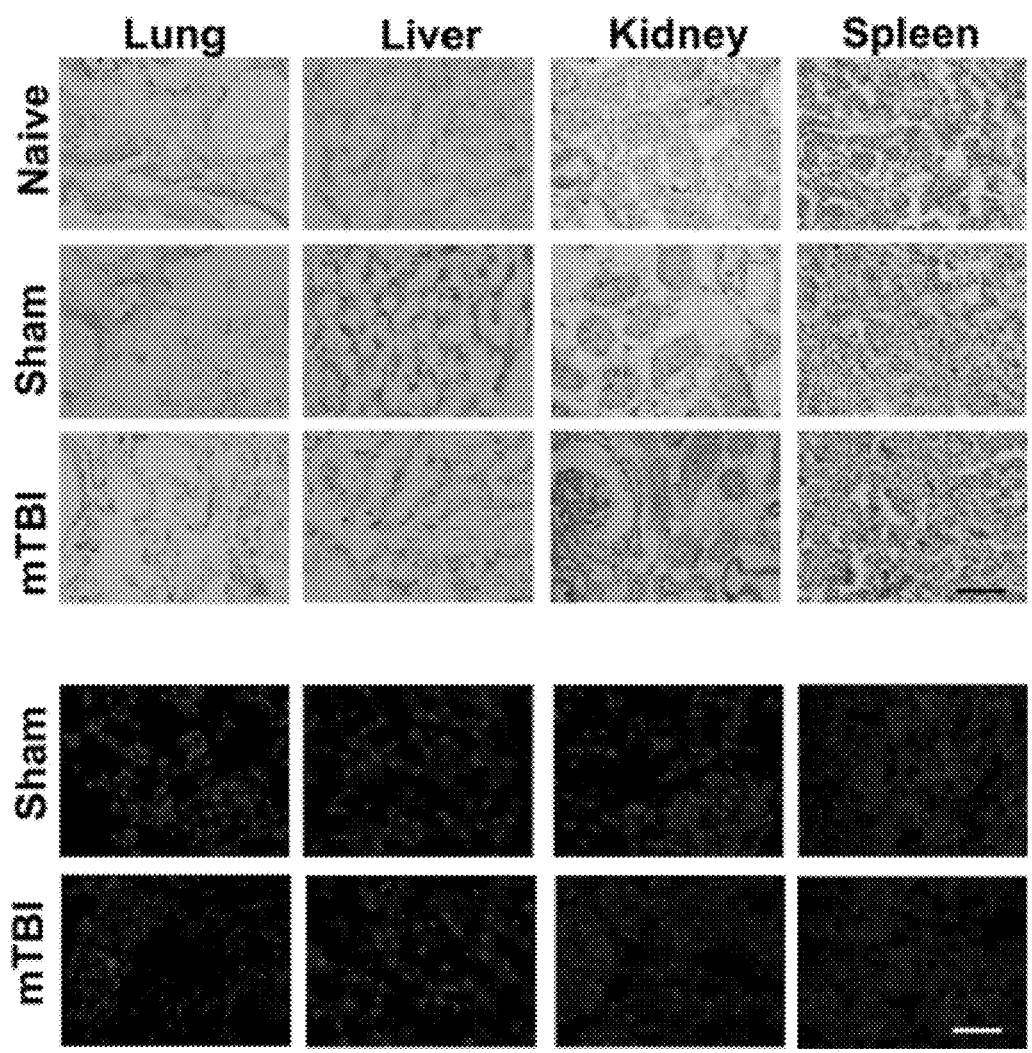
Figure 3C:
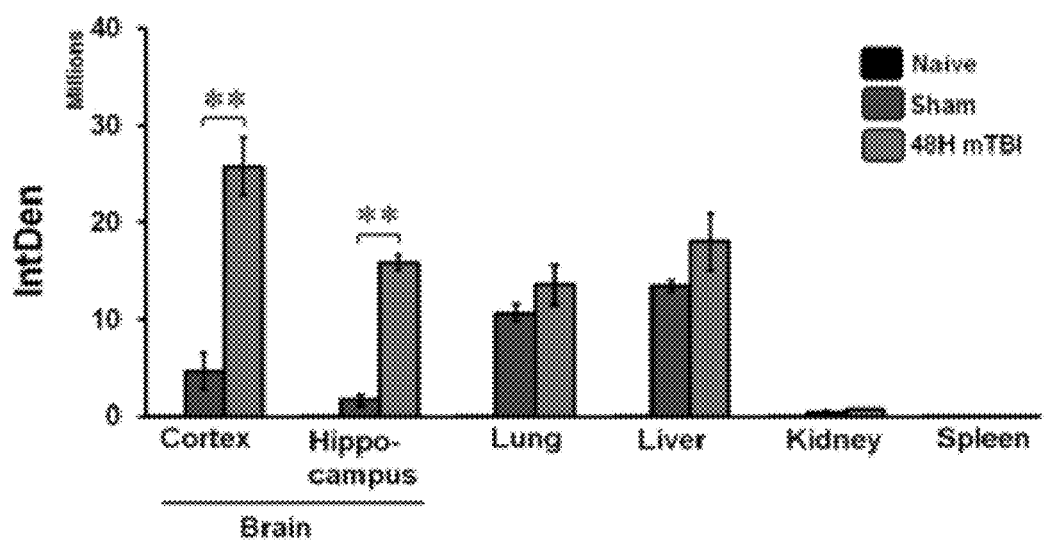

PB staining was performed on lung, liver, kidney and spleen sections to determine if 4MNP nanoparticles were present in those organs (FIG. 3B, upper panels). PB staining was undetectable in the naïve animals that received no 4MNPs. In sham-operated animals insignificant labeling was observed in lung and liver after 48 hours of administration. The spleens of these animals showed some PB-positive particles but most of the particles were observed in the kidneys, indicating their excretion from the body. In the animals given mTBI, large amounts of PB-positive particles were seen in the lung, liver, kidney and spleen 48 hours after administration. The lungs contained the least amount of 4MNP particles while liver and kidney had higher concentrations. These findings suggest that 4MNP nanoparticles get excreted from the body rapidly, and healthy rats excrete these nanoparticles from the body faster than those with mTBI. Also, it was observed that among these tissues only lung and liver showed RFP expression in both sham and mTBI animals. Although spleen and kidney showed the presence of substantial amounts of iron-oxide particles, no RFP expression was observed in these organs (FIG. 3B, lower panels). A comparative analysis of the RFP expression in the brain (cortex and hippocampus), lung, liver, spleen and kidney showed the highest expression in the cortex. RFP expressions in the cortex and hippocampus were significantly higher than the corresponding areas of the sham animals. On the other hand, although lung and liver showed RFP expression, there was not much difference between sham and mTBI animals (FIG. 3C).

Example 6 mTBI causes Blood-Brain Barrier Disruption and 4MNP Entry into the Brain

Figure 4:
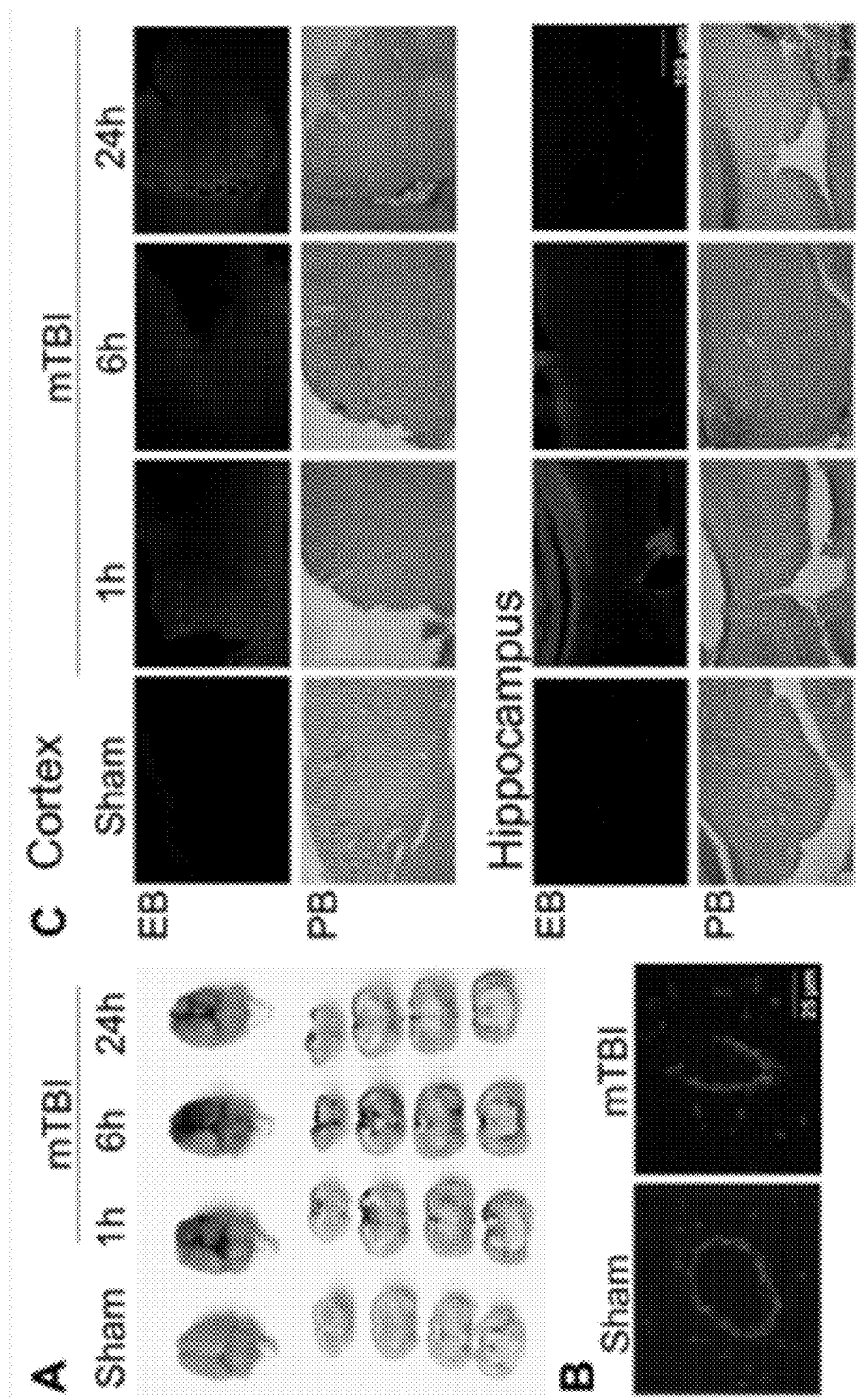
FIG. 4 (A-C) shows that maximum extravasation is observed 6 hours after mTBI. The upper panel of FIG. 4A pictures the dorsal surface of the whole brain showing the spread of the Evans blue dye. Lower panels demonstrate 4 mm thick coronal sections from the same brains showing the internal spread of EB.

An Evans blue (EB) extravasation study showed EB entry in the brain parenchyma within 1 hour of mTBI. EB entry was also observed at 24 hours of mTBI although maximum intensity and penetration into the tissue, as seen in the coronal sections, was observed at 6 hours post-TBI. On the other hand, the sham animals did not show any EB entry in the brain (FIG. 4 A).

Protocols for the EB study were as follows: LFPI was induced in rats or sham surgery was performed as described above. Rats were allowed to survive for 1 hour, 6 hours, or 24 hours. 30 minutes before euthanasia, 2% Evans Blue solution was injected through the tail vein. At the same time, 2.5 µg/ml 4MNP solution was instilled intranasally at a dose of 50 µl/nostril. Rats were deeply anesthetized and 0.9% saline solution was infused transcardially and continued as long as colored solution was coming out of the right atrium. Rats were then perfused with 4% PFA solution and tissues were collected.

For tissue collection, rats were deeply anesthetized with ketamine (75 mg/kg) and xylazine (7.5 mg/kg) 24 or 48 hours after MTBI and then perfused with 0.9% saline followed by 4% paraformaldehyde (PFA) in phosphate buffer. The Evans Blue injected rats were perfused with 0.9% saline until the clear fluid came out of the right atrium and then perfused with 4% PEA. The brain, lungs, liver, kidneys and spleen were removed, post-fixed in 2% PFA and saturated with increasing sucrose concentrations (20% to 30%) in PBS. Tissues were then frozen in OCT. Brains were sectioned coronally at 30 µm thickness, thaw-mounted onto glass slides and stored at −20° C. prior to staining. All other tissues were sectioned at 5 µm thickness, thaw-mounted on glass slides and stored at −20° C. for future use.

Confocal microscopic images of cerebral micro-vessels immunostained with antibody against smooth muscle actin (SMA) were also obtained and showed disrupted microvasculature in mTBI rats (FIG. 4B). This assay was performed as follows: Slide-mounted tissue sections were washed with PBS for 5 minutes, incubated in 3% hydrogen peroxide for 20 minutes and washed 3 times in PBS. They were then heated in 1% antigen-unmasking solution (Vector Laboratories Inc, Burlingame, Calif.) for 20 minutes at 90° C., incubated for 1 hour in permeabilization buffer (10% goat serum, 0.1% Triton X-100 in PBS) and incubated overnight at 4° C. with rabbit anti-IL-1β (1:100) or mouse anti-IL-6 (1:100) or mouse anti-TNFα (1:50) antibodies (Abcam, Cambridge, Mass.) in antibody solution (5% goat serum, 0.05% Triton X-100 in PBS). The next day, the sections were washed with PBS and incubated 1 hour at room temperature with biotinylated goat anti-rabbit, (1:400), or biotinylated goat anti-mouse (1:400) antibodies (Vector Laboratories Inc., Burlingame, Calif.) in antibody solution. Sections were then washed in PBS, incubated in avidin-biotin complex mixture (ABC, 1:100; Vector Laboratories Inc, Burlingame, Calif.) for 1 hour at room temperature, washed again and developed with diaminobenzidine solution (DAB), washed with PBS, dried and cover slipped with vectamount mounting medium.

The above observations clearly indicate the disruption of the BBB following mTBI in these studies. Simultaneous EB extravasation and intranasal 4MNP administration experiments revealed the localization of 4MNP nanoparticles (PB staining) in the same areas of the cortex and hippocampus where EB fluorescence was also observed. Since EB and PB staining were absent in the sham animals, and it is known that EB enters the brain parenchyma via the ruptured blood vessels, these findings clearly suggest that 4MNP nanoparticles entered the brain parenchyma via the compromised cerebral microvasculature.

Example 7

4MNP does not Evoke Inflammatory Response in Rats

Figure 5:
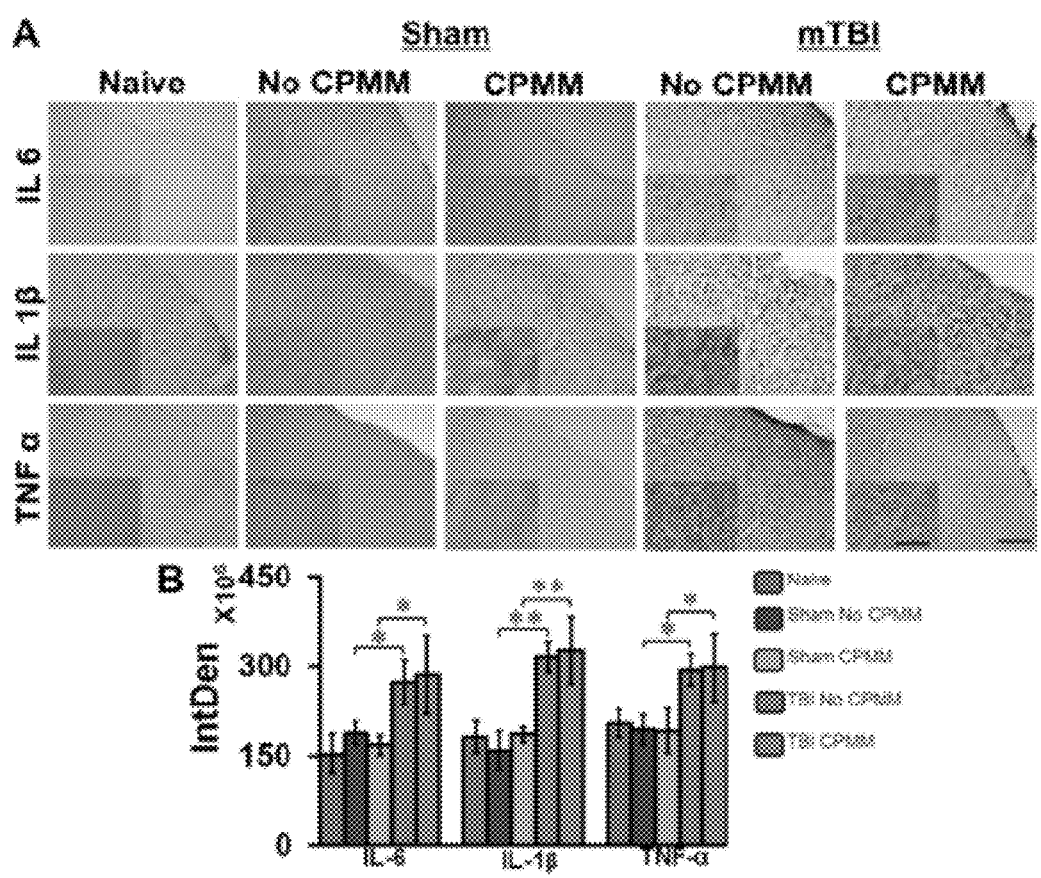
FIG. 5 (A-B) shows that 4MNP does not evoke an inflammatory response in rats. Brain sections from naïve, sham or mTBI rats were immunostained for IL-6, IL-1b or TNF-a.

Naïve or 4MNP treated sham or mTBI animals euthanized 24 hours after mTBI were used to study the inflammatory response, if any, evoked by the 4MNP particles. Brain sections were stained with antibodies against early inflammatory markers interleukine-6 (IL-6), interleukine-1β or tumour necrosis factor-α (TNF-α). The levels of cytokines expression did not change in either naïve or sham animals, although changes were observed in mTBI animals (FIG. 5A). Measurement of the integrated density of the immune-reactivity by image J showed no changes in IL-6, IL-1β or TNF-α expression in naïve or sham animals and significant increase in mTBI animals irrespective of whether they were treated with 4MNP or not (FIG. 5B). These observations clearly indicate that the 4MNP nanoparticles are non-inflammatory.

The invention claimed is:

1. A method of transfecting a brain cell of a subject in need thereof with a polynucleotide comprising:
systemically administering to the subject in need thereof a composition comprising a micelle having a hydrophobic superparamagnetic iron oxide nanoparticle (SPION) core, a first coating comprising a cationic polymer, and a second coating comprising the polynucleotide, wherein the subject in need thereof has a mild traumatic brain injury (TBI), wherein the first coating comprises a chitosan and a polyethyleneimine (PEI), and wherein the chitosan has a chemical formula of:

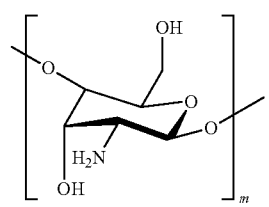

wherein "m" is between 1 and 1,000;
and wherein the PEI has a chemical formula of:

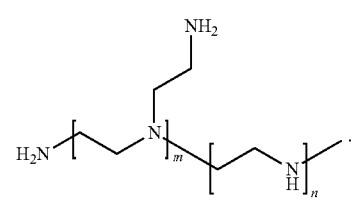

wherein "m" is between 1 and 1,000, and "n" is between 1 and 1,000, and wherein the SPION core comprises a coating of oleic acid and oleylamine.

2. The method of claim 1, wherein the micelle comprises multiple copolymers having a chemical formula of:

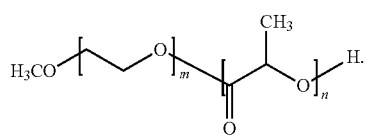

III wherein "m" is between 1 and 1,000, "n" is between 1 and 1,000.

3. The method of claim 1, wherein the SPION core is prepared using iron, 1,2-dodecanediol, oleic acid, oleylamine, and benzyl ether.

4. The method of claim 2, wherein a molar weight ratio of the chitosan and the polynucleotide is between approximately 3:1 and 7:1.

5. The method of claim 2, wherein a molar weight ratio of the PEI and the polynucleotide is between approximately 7:1 and 3:1.

6. The method of claim 2, wherein a molar weight ratio of chitosan and PEI is between approximately 3:7 and 7:3.

7. The method of claim 6, wherein a molar weight ratio of chitosan and PEI is approximately 5:5.

8. The method of claim 7, wherein a molar weight ratio of chitosan, PEI and polynucleotide is approximately 5:5:1, respectively.

9. The method of claim 1, wherein the subject is a human.

10. The method of claim 1, wherein the composition is administered intranasally.

11. The method of claim 10, wherein a cortex brain cell is transfected.

12. The method of claim 11, wherein a hippocampal brain cell is transfected.

13. The method of claim 1, wherein the composition is administered up to 24 hours after commencement of the mild TBI.

* * * * *